United States Patent
Förster et al.

(10) Patent No.: US 9,603,725 B2
(45) Date of Patent: *Mar. 28, 2017

(54) PROSTHESIS ASSEMBLY WITH ADJUSTABLE DIAMETER SOCKET

(71) Applicant: OTTO BOCK HEALTHCARE GMBH, Duderstadt (DE)

(72) Inventors: Heiko Förster, Duderstadt (DE); Christian Heublein, Duderstadt (DE)

(73) Assignee: OTTO BOCK HEALTHCARE GMBH, Duderstadt (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/348,980

(22) PCT Filed: Oct. 2, 2012

(86) PCT No.: PCT/EP2012/004125
§ 371 (c)(1),
(2) Date: Apr. 1, 2014

(87) PCT Pub. No.: WO2013/050135
PCT Pub. Date: Apr. 11, 2013

(65) Prior Publication Data
US 2014/0243996 A1    Aug. 28, 2014

(30) Foreign Application Priority Data
Oct. 6, 2011    (DE) .................. 10 2011 114 920

(51) Int. Cl.
*A61F 2/80*    (2006.01)
*A61F 2/60*    (2006.01)
(Continued)

(52) U.S. Cl.
CPC .................. *A61F 2/80* (2013.01); *A61F 2/60* (2013.01); *A61F 2/72* (2013.01); *A61F 2/7812* (2013.01);
(Continued)

(58) Field of Classification Search
CPC .. A61F 2/72; A61F 2/7812; A61F 2/78; A61F 2/80; A61B 5/04888
See application file for complete search history.

(56) References Cited

U.S. PATENT DOCUMENTS

| 5,413,611 A | 5/1995 | Haslam, II et al. |
| 5,443,525 A | 8/1995 | Laghi |

(Continued)

FOREIGN PATENT DOCUMENTS

| DE | 102005021412 A1 | 11/2006 |
| DE | 202006007460 U1 | 10/2007 |

(Continued)

OTHER PUBLICATIONS

Advances in Myoelectrics by Ottobock. O&P Edge Magazine. Dec. 2004.*

(Continued)

*Primary Examiner* — Marcia Watkins
(74) *Attorney, Agent, or Firm* — Holland & Hart LLP

(57) ABSTRACT

The invention relates to a prosthesis assembly, comprising an outer stem (10) provided with a proximal opening (11), and at the distal end (12) thereof is provided with a connecting means (13) for fastening an additional component, and which is formed of a material that is rigid in the longitudinal extension thereof, in which at least one slit (14) extending at least partially in a longitudinal direction is inserted in order to allow deformation in a radial direction. The prosthesis assembly further comprises an inner stem (20) made of a flexible material and provided with a proxi- (Continued)

mal opening (21), at least one tensioning device (30) that is affixed to the outer stem (10) and can be accessed by way of a diameter change of the outer stem (10). At least one electrode (40) is displaceably fastened to a side of the outer stem (10) that is facing the inner stem (20).

22 Claims, 5 Drawing Sheets

(51) Int. Cl.
*A61F 2/72* (2006.01)
*A61F 2/78* (2006.01)
*A61F 2/50* (2006.01)
*A61B 5/0488* (2006.01)
*A61F 2/54* (2006.01)
*A61F 2/76* (2006.01)

(52) U.S. Cl.
CPC ............ *A61B 5/04888* (2013.01); *A61F 2/54* (2013.01); *A61F 2002/502* (2013.01); *A61F 2002/5021* (2013.01); *A61F 2002/5027* (2013.01); *A61F 2002/5084* (2013.01); *A61F 2002/7615* (2013.01); *A61F 2002/7862* (2013.01)

(56) References Cited

U.S. PATENT DOCUMENTS

| | | |
|---|---|---|
| 2004/0158332 A1 | 8/2004 | Carstens |
| 2007/0265711 A1 | 11/2007 | Klein |
| 2009/0216339 A1 | 8/2009 | Hanson et al. |
| 2010/0030341 A1 | 2/2010 | Dietl et al. |
| 2010/0274364 A1* | 10/2010 | Pacanowsky et al. .......... 623/36 |
| 2011/0134139 A1 | 6/2011 | Brandmayr et al. |
| 2012/0101596 A1 | 4/2012 | Dietl |
| 2014/0018938 A1* | 1/2014 | Bertels et al. .................. 623/25 |

FOREIGN PATENT DOCUMENTS

| | | |
|---|---|---|
| DE | 102008036714 A1 | 2/2010 |
| DE | 102009030217 A1 | 1/2011 |
| EP | 1411872 B1 | 12/2004 |
| GB | 1191633 | 5/1970 |

OTHER PUBLICATIONS

PCT International Search Report for PCT International Patent Application No. PCT/EP20121004125, mailed Jan. 8, 2013.

* cited by examiner

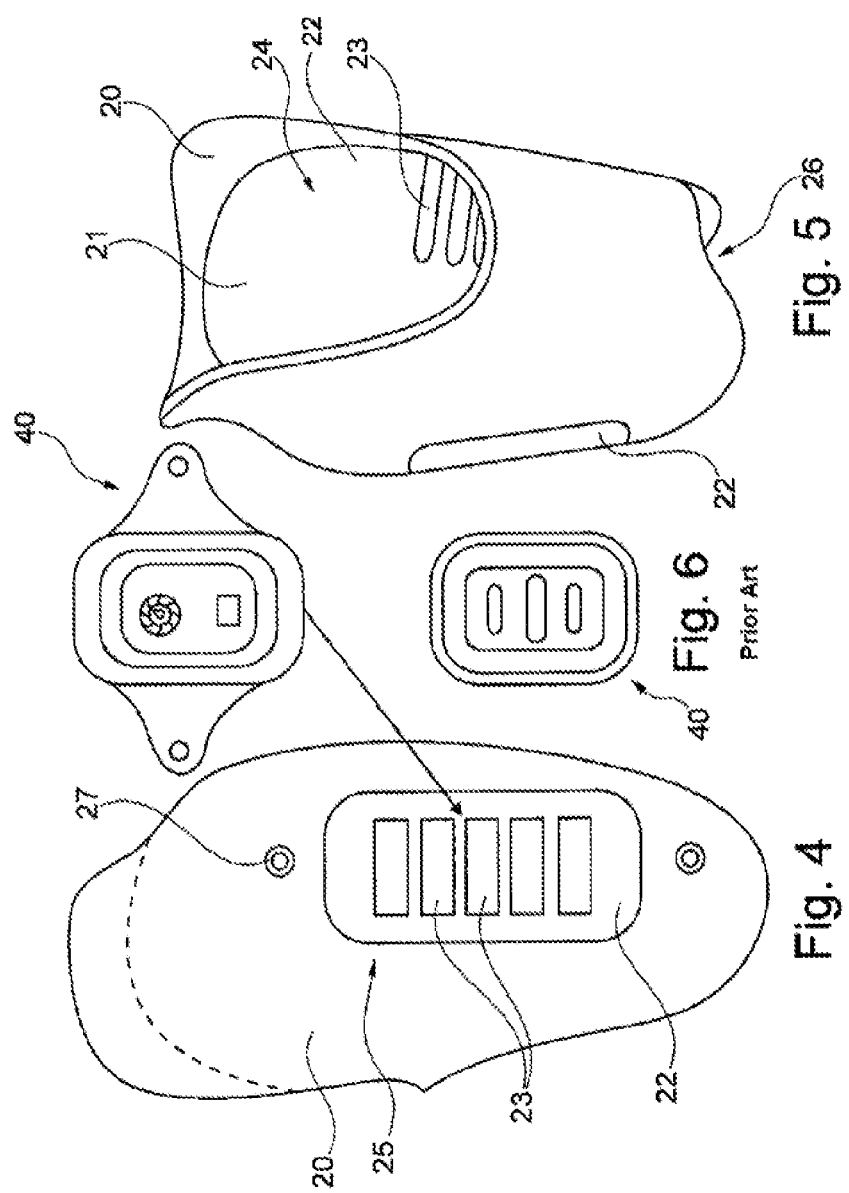

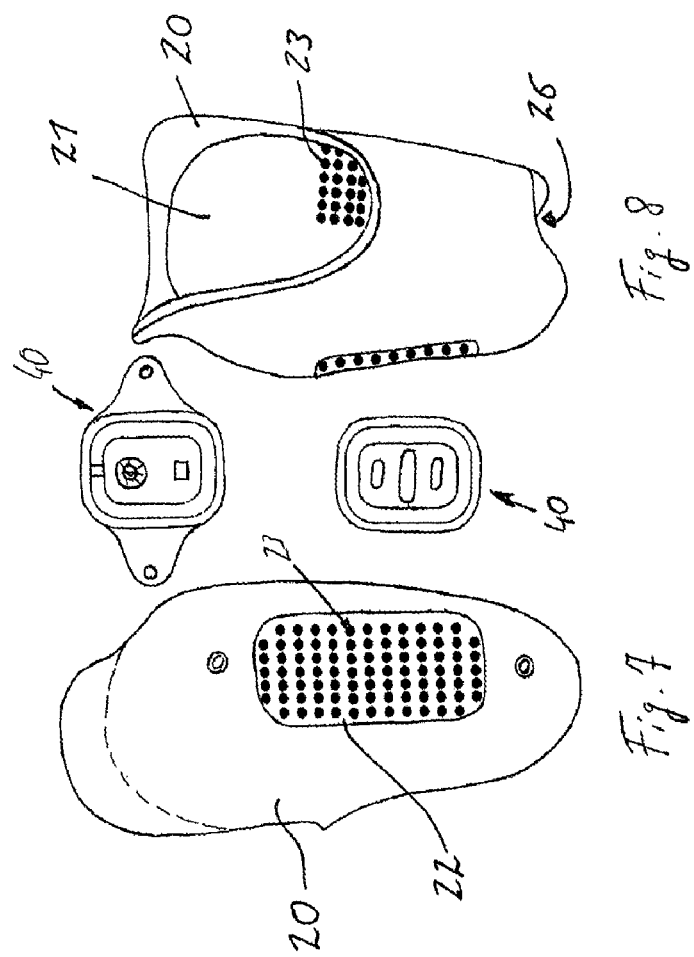

PROSTHESIS ASSEMBLY WITH ADJUSTABLE DIAMETER SOCKET

TECHNICAL FIELD

The invention relates to a prosthetic appliance comprising an outer socket, which has a proximal opening and, at the distal end thereof, connection means for fastening an additional component, and is formed from a material rigid in the direction of longitudinal extent, wherein at least one slit extending at least partially in the direction of longitudinal extent is introduced into said outer socket in order to enable a deformation in the radial direction, an inner socket, which is formed from a flexible material and has a proximal opening, and at least one tensioning appliance, which is fixed on the outer socket and by means of which a change in diameter of the outer socket is achievable. Such a prosthetic appliance is advantageous, in particular for so-called test prostheses or interim prostheses, which are not individually adapted by molding the amputation stump.

BACKGROUND

Prostheses have been known for a long time and serve to replace non-existent, e.g. lost limbs. Functional elements, e.g. prosthetic hands or prosthetic feet, are in this case fastened to a dimensionally stable outer socket, which surrounds the amputation stump on all sides and generally has a funnel-shaped embodiment. The outer socket serves to transmit the force from the amputation stump to the functional element. Outer sockets are produced from fiber reinforced plastics, wood or metal and are regularly adapted as precisely as possible to the amputation stump in order, in addition to a high comfort of wear with an ideal support effect, to be able to produce, inter alia, a negative pressure so as to be able to keep the prosthetic socket on the amputation stump.

The problem lies in the fact that the volume of an amputation stump varies over time; for example, an amputation stump initially swells up after the amputation or after surgery and then the swelling reduces again. However, a goal of prosthesis care lies in accustoming the patients as quickly as possible to the prosthetic provision. In order to enable, within predetermined boundaries, an adaptation to amputation stumps with changing diameters and lengths, EP 1 411 872 B1 describes a prosthesis which describes a silicone liner with a coupling pin, a prosthetic socket, which has been provided with longitudinal slits and the diameter of which can be changed by means of tensioning elements, and a holder for connecting an artificial limb to the prosthetic socket, in which the longitudinal slits are bypassed. The prosthetic socket has a concentric collar, in which a cylindrical adapter is fastened in a height-adjustable manner.

SUMMARY

It is an object of the present invention to provide a prosthetic appliance, by means of which it is possible to carry out first care for different patients in a quick and simple manner, even with driven components or functional elements, which are fastened to the outer socket and controlled by myoelectric signals.

According to the invention, this object is achieved by a prosthetic appliance with the features of the main claim; advantageous embodiments and developments of the invention are disclosed in the dependent claims, the description and the figures.

The prosthetic appliance according to the invention, comprising an outer socket, which has a proximal opening and, at the distal end thereof, connection means for fastening an additional component, and is formed from a material rigid in the direction of longitudinal extent, wherein at least one slit extending at least partially in the direction of longitudinal extent is introduced into said outer socket in order to enable a deformation in the radial direction, an inner socket, which is formed from a flexible, optionally elastic and stretchable material and has a proximal opening, and at least one tensioning appliance, which is fixed on the outer socket and by means of which a change in diameter of the outer socket is achievable, provides for at least one electrode to be displaceably fastened on a side of the outer socket facing the inner socket.

Displaceably fastening an electrode to the inner side of the outer socket renders it possible to perform a quick and simple option for testing myoelectric care on a patient, without needing to take a print of the amputation stump in a complicated manner and without an electrode having to be installed in the outer socket with much effort. This renders it possible, even without the provision of an individual prosthetic appliance, to perform test care, and so, for example, suitable prosthetic components such as driven prosthetic hands or prosthetic knee joints can be examined in respect of suitability in principle prior to the final adaptation of the outer socket. This renders it possible to avoid high costs in patient care, since it is already possible to check in advance whether and which driven prosthetic component, which can be fastened to the outer socket, is suitable, how the electrodes are to be arranged and where there can be an advantageous arrangement of the electrodes for controlling the components.

A development of the invention provides for at least one area with conductive elements to be provided on the inner socket, which conductive elements conduct myoelectric signals from the inner side of the inner socket to the outer side of the inner socket. By providing at least one area with conductive elements or made of a conductive material, which conducts myoelectric signals from the skin surface of the amputation stump to the outer side of the inner socket, it is possible to cover a relatively large skin surface area suitable for deriving myoelectric signals. It is no longer necessary to position and to affix surface electrodes on the skin surface with much difficulty and then to forward the signals by means of cables to a control appliance; rather, approximate positioning of the area with conductive elements renders it possible to cover a large area of possible myoelectric signal sources without much effort, with said area then being assigned to the electrode arranged on the outer socket. The assignment between the electrode and the area with conductive elements or made of conductive material is then brought about in accordance with the stipulation of the type of signal and the quality of the signal, i.e. to what muscle the signal can be assigned or what signal strength is present.

The conductive elements can be embedded in the inner socket or the area of regions can be embodied from a conductive plastic. In principle, it is also possible to form the whole inner socket from a conductive material, in which regions are electrically separated from one another by insulation sections such that myoelectric signals can be recorded along a very large surface. As a result, it is possible to undertake a fast and simple adaptation of myoelectric electrodes since the electrode or electrodes arranged on the outer socket can be positioned in an easily changeable manner. The positioning can be changed even when the prosthetic appliance is still applied, for example if the tensioning appliance is loosened such that the outer socket can be bent open radially to the outside.

The inner socket can be affixed to the outer socket; advantageously, the inner socket is affixed permanently to the outer socket such that the prosthetic appliance can be handled as a system of inner socket, outer socket and tensioning appliance together with the optionally likewise permanent but displaceable electrode arranged on the outer socket. The inner socket is advantageously arranged on the outer socket in such a way that, in the case of a restricted area with conductive elements or made of a conductive material, said area is arranged in such a way that it is possible to derive myoelectric signals and that there is a spatial assignment between the electrode and the area.

The inner socket advantageously has a closed cross section such that it can easily be placed onto the amputation stump due to the stretchable and elastic material. Therefore, the inner socket is embodied as a variable, adaptable but nevertheless secure inner socket, which forms the interface to the amputation stump. The maximum stretchability of the inner socket is advantageously adapted to the radial flexibility of the outer socket, and so, optionally, provision can be made for pre-manufactured sizes with different diameter gradings. Thus, prosthetic appliances with different sizes can be prepared for different patient types, which sizes cover the whole or almost the whole size range of the patients to be cared for.

The inner socket can have an open distal end such that, as a result of the opening, firstly, no pressure is exerted on the distal stump end and, secondly, it is also possible to adapt the length in the proximal direction by displacing the inner socket on the amputation stump.

The inner socket is advantageously formed from silicone and can, in regions, consist of a conductive silicone or a mixture of a silicone and a different plastic or conductive material. The outer socket advantageously consists completely of a fiber reinforced plastic.

The electrode between the inner socket and the outer socket can be displaceably and/or rotatably mounted in at least one guide which is arranged or formed on the outer socket. It is likewise possible for the electrode to be fastened to the inner side of the outer socket by a special surface embodiment by means of an interlocking element, e.g. a hook-and-loop lock.

The electrode is advantageously displaceably mounted in the direction of longitudinal extent and in the circumferential direction of the outer socket, and so the electrode or the electrodes can be positioned relatively freely on the outer socket.

Locking appliances can be embodied as tape or belt and set the maximum change in diameter of the outer socket. To this end, the tape or the belt has a closed embodiment or is fastened to the outer socket in such a way that removal or separation of the tape or of the belt is not possible, and so the outer socket and hence also the inner socket cannot be bent open beyond a provided limit. The tensioning appliance also sets the maximum change in diameter during a compression. The tensioning appliance can have a ratchet lock, a lever lock, a rotary clamping lock and/or a hook-and-loop lock; for example, the ratchet lock can be embodied as a rotatable lock which causes a tensioning effect by rotation in one direction and enables loosening by a different actuation.

The material of the inner socket can be embodied to be elastic and stretchable or, as an alternative thereto, the inner socket can have a slit in the direction of longitudinal extent. A lateral opening in the inner socket can enable a circumferential adaptation. Overlapping sections, which possibly have a reduced material strength in the region of overlap such that a substantially unchanging material strength can be maintained, likewise meet the requirements placed on a circumferential adaptability. To this end, it is also possible for elastic and stretchable inserts to be introduced into the inner socket.

The slit in the outer socket can be partly or completely filled by an elastic material, e.g. an elastomer, in order, for example, to avoid clamping of the inner socket therein without impairing the ability of the outer socket to be opened up. The elastomer can likewise influence the deformation resistance.

BRIEF DESCRIPTION OF THE DRAWINGS

In the following text, an exemplary embodiment of the invention will be explained in more detail on the basis of the attached figures. In detail:

FIG. 4 shows a side view of an inner socket;
FIG. 5 shows a front view of an inner socket;
FIG. 6 shows views of an electrode;
FIG. 7 shows a side view of a variant of the inner socket;
and
FIG. 8 shows a front view of the variant as per FIG. 7.

DETAILED DESCRIPTION

Figure 1:
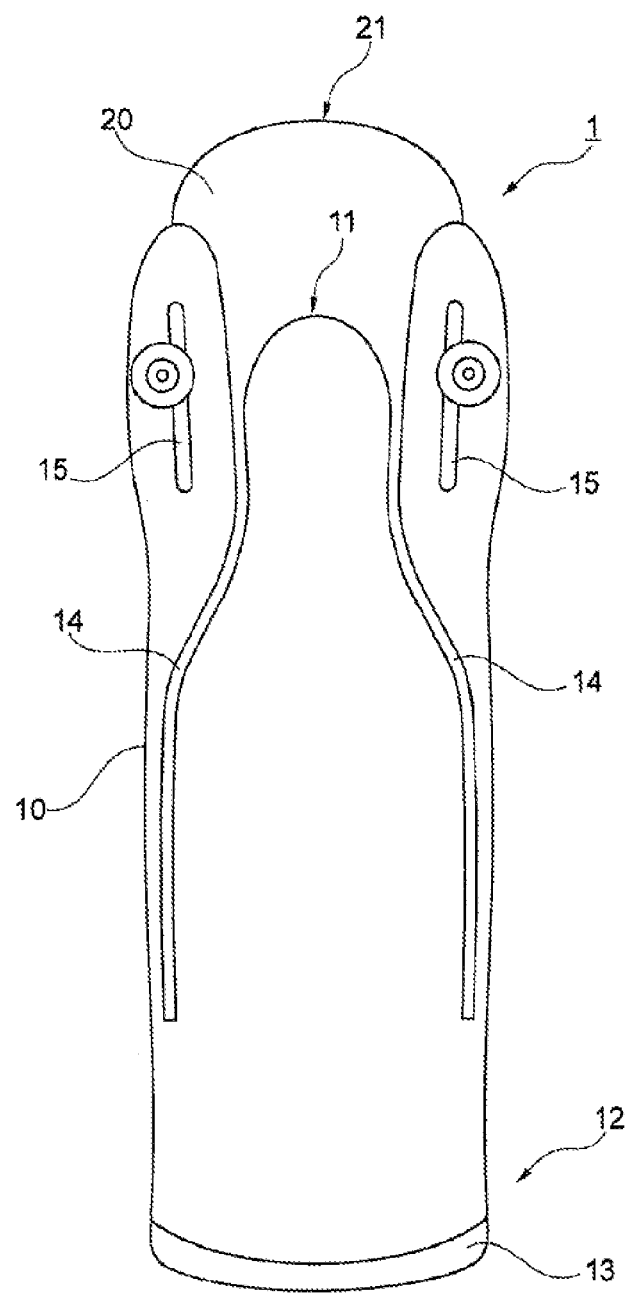
FIG. 1 shows a rear view of a prosthetic appliance.

FIG. 1 depicts a rear view of a prosthetic appliance 1 in the form of a forearm prosthesis. The prosthetic appliance 1 has an outer socket 10 and, arranged therein and fastened thereto, an inner socket 20. In the depicted exemplary embodiment, the prosthetic appliance 1 is worn on a forearm stump; the forearm stump is not depicted here. Alternatively, applying the prosthetic appliance 1, the forearm stump is introduced into the inner socket 20 through a proximal opening 21 and the inner socket 20 with the forearm stump is subsequently introduced into a proximal opening 11 of the outer socket 10 and affixed thereto.

The outer socket 10 consists of a material that keeps its form, preferably a fiber-reinforced plastic, in which fiber mats, e.g. glass-fiber mats or carbon fiber mats, have been embedded in a plastic matrix. This composite material renders it possible to achieve high strength with low wall thicknesses, while at the same time having a low weight. In the direction of longitudinal extent of the outer socket 10, very rigid properties are realized by means of this material; compressing or elongating or stretching of the outer socket 10 is not possible along the direction of longitudinal extent, or only to an extremely small extent. The outer socket 10 has a substantially cylindrical set up and, in terms of its contour, substantially corresponds to the contour of a forearm. Connection means 13 for further components, for example a prosthetic hand or the like, are provided at the distal end 12 of the outer shaft 10. There can be secure coupling between the additional components and the prosthetic appliance 1 by means of the connection means 13. The connection means 13 enable reversible fastening of the additional component so as to allow an adaptation to the respective usage purpose.

Slits 14 have been worked into the outer frame 10, which slits are substantially arranged in the direction of longitudinal extent of the prosthetic appliance 1. The slits 14 extend with substantial folding symmetry with respect to a folding axis (not depicted here), which extends along the direction of longitudinal extent of the outer socket 10; deviating profiles are possible and envisaged. The slits 14 end before the distal end 12 of the outer socket 10, and so there is a substantially closed cross section of the outer socket 10 in a tubular form at the distal end 12. The slits 14 enable mobility of the outer socket 10 in the radial direction. The segments of the outer socket 10 formed by the slits 14, which segments are interconnected at the distal end 12, can therefore be displaced inwardly and outwardly in the radial direction, with the outer socket 10 preferably having an elastic embodiment in the radial direction such that, when proceeding from an initial position, a resistive force has to be overcome when bending open or pressing together the segments.

Furthermore, guides 15 in the form of slits are provided on the outer socket 10; these guides are likewise arranged with an orientation substantially along the direction of longitudinal extent of the outer socket 10 in the depicted exemplary embodiment. The guides 15 can also be embodied as open slits, i.e. not be completely surrounded by the material of the outer socket 10; it is likewise possible for the orientation of the guides 15 to extend in the circumferential direction or to describe a curve.

The inner socket 20 with the proximal opening 21 can be securely fastened to the outer socket 10, for example by means of rivets, screws, interlocking elements or the like; as an alternative thereto, a shaping of the outer socket 10 can bring about interlocking latching of the inner socket 20 to the outer socket 10. The inner socket 20 is preferably formed from silicone; alternative materials can be envisaged. The length of the inner socket 20 depends on the length of the outer socket 10 and on the length of the stump to be cared for. The inner socket 20 usually ends before the distal end 12 of the outer socket 10. The inner socket 20 advantageously has a closed cross section, but it can also have an open distal end such that length variations of the stump to be cared for can be compensated for and that moreover no pressure is exerted on the possibly still sensitive distal end of the stump. The material of the inner socket 20 is advantageously embodied to be elastic and stretchable; it is likewise possible for there to be a slit in the direction of longitudinal extent of the inner socket 20 such that the inner socket 20, at least in sections, consists of two plies overlapping one another. Compared to the remaining material of the inner socket 20, these plies can have a thinner form so that there is no material thickening in the region of the coverage.

Figure 2:
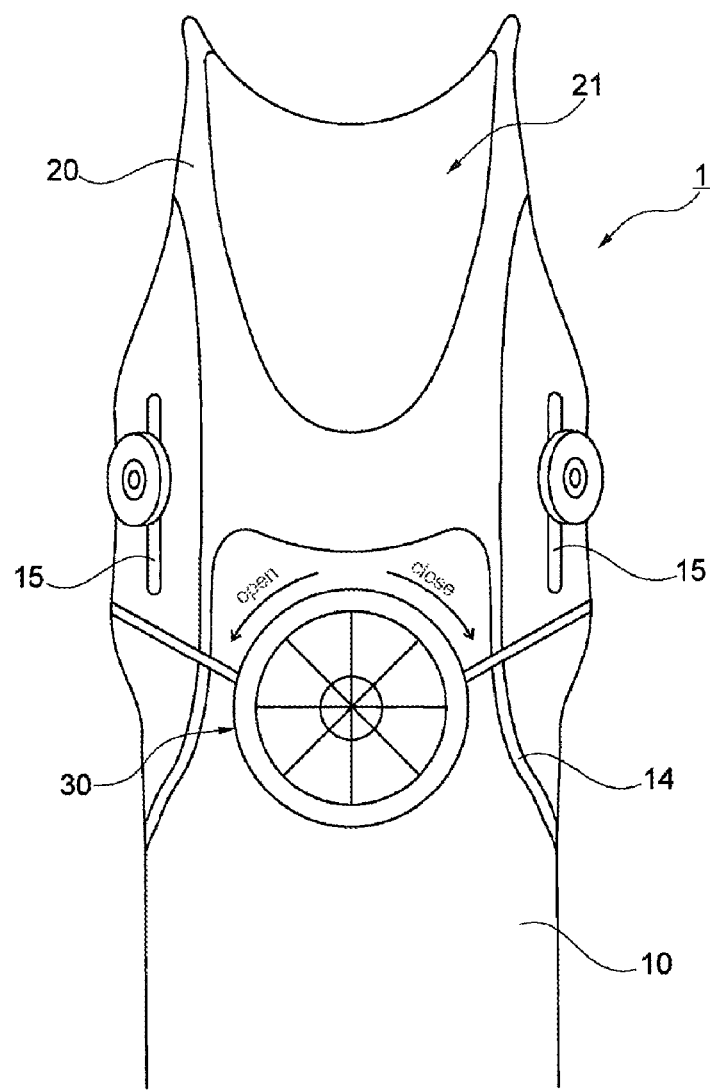
FIG. 2 shows a front view of a prosthetic appliance.

FIG. 2 depicts the prosthetic appliance 1 in a front view. It is possible to identify both the inner socket 20 with the proximal opening 21 and the outer socket 10 with the slits 14 extending in the direction of longitudinal extent and the guides 15, which are arranged medially and laterally. Complementing FIG. 1, FIG. 2 depicts a tensioning appliance 30 in the form of a rotary clamping lock, by means of which it is possible to change the diameter of the outer socket. By rotation in one direction or the other, it is possible to close or open the tensioning appliance 30 by lengthening or shortening the tapes or cables associated with the tensioning appliance 30. Due to the slits 14 extending in the direction of longitudinal extent of the outer socket 10, four separate segments result in the proximal region of the outer socket 10, which segments are oriented in the medial, lateral, dorsal and ventral directions. It is possible to identify in FIG. 2 that the rotary clamping lock 30 is arranged on the side of the outer socket 10 arranged ventrally, i.e. on the segment facing the bend of the elbow.

The inner socket 20 can consist of a plastic or silicone which, in different regions, has different Shore-hardness values such that the stump to be held therein is embedded ideally.

By means of the rotary clamping lock 30 it is possible to bring about a change in the circumference of the tensioning means such that a force acting in the radial direction is applied to the outer socket 10, the inner socket 20 and, thereby, onto the stump. This renders it possible to set the prosthetic appliance 1 individually to the stump of the user of the prosthetic appliance 1 by means of the tensioning appliance 30 and thus adapt it to said user. This appliance renders it possible to store a pre-manufactured outer socket 10 or a plurality of outer sockets in standard sizes and then adapt this individually to the patient, and so the expensive and complicated individual adaptation by taking a plaster cast and manufacturing a prosthetic socket with fiber-reinforced composite materials is not necessary. Such a prosthetic appliance can preferably be used as a so-called test prosthesis such that the suitability in principle of such a prosthetic appliance for a patient can be examined without great financial outlay. Such a test prosthetic appliance is particularly advantageous for patients who, for the first time, are equipped with a driven prosthetic appliance controlled by myoelectric signals.

Figure 3:
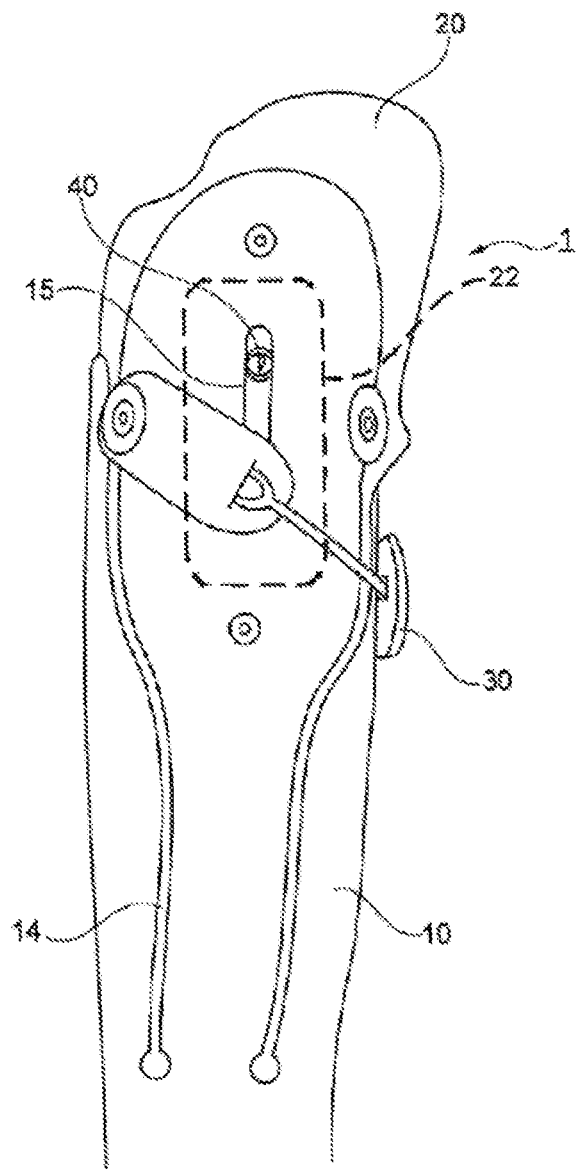
FIG. 3 shows a side view of a prosthetic appliance.

FIG. 3 depicts a side view of the prosthetic appliance 1 having the outer socket 10, the inner socket 20 and the tensioning appliance 30. FIG. 3 shows that an electrode 40 is guided in a displaceable manner in the guides 15 of the segments oriented medially and laterally. A bolt or pin is fastened to the electrode 40 and protrudes through the guide 15 embodied as a slit to the outer side of the outer socket 10 such that the electrode 40 is arranged between the inner side of the outer socket 10 and the outer side of the inner socket 20. The electrode 40 can be moved along the guide 15, presently substantially along the direction of longitudinal extent of the outer socket 10. The electrode 40 can be rotatably mounted within the guide 15 such that the electrode 40 can be arranged ideally on the patient. By fastening appliances, e.g. threaded screws, wedges, clips or the like, it is possible to affix the electrode 40 on the outer socket 10 in the position considered to be expedient.

It is furthermore possible to identify in FIG. 3 that the tensioning means 30 is substantially guided circumferentially around the outer socket 40. Thus, two belts of the rotary clamping lock 30 can be guided around the outer socket in the circumferential direction and fastened to the opposite segment, in this case the dorsal end segment. By rotation in the clockwise direction, the tension on the tensioning means is increased, and so there can be a change in diameter of the outer socket 10 by displacing the segments separated by the slits 14. If the rotary clamping lock 30 is actuated in the counterclockwise direction, the outer socket 10 is sprung back into the initial position. Locking appliances can be provided to avoid excessive widening of the outer socket 10 and of the inner socket 20. To this end, the tensioning appliance 30 can be equipped with an end stop such that when a maximum widening is reached, a locking effect occurs; alternatively, a separate locking appliance is possible.

FIG. 4 shows the inner socket 20 in a side view. The inner socket 20 has an area 22 on the medial side of the inner socket 20, in which a multiplicity of 15 conductive elements 23 are arranged. In the depicted exemplary embodiment, the conductive elements 23 are embodied as parallel, substantially rectangular elements 23, by means of which myoelectric signals from the skin surface can be conducted from an inner side of 20 the inner socket 20 to an outer side 25 of the inner socket 20. Provision is likewise made for fastening elements 27 on the inner socket, by means of which fastening elements the inner socket 20 can be fastened to the outer socket 10.

FIG. 5 shows a front view of the inner socket 20 with the proximal opening 21 and the distal opening 26. It can be gathered from FIG. 5 that the conductive elements 23 also protrude through the surface of an inner side 24 of the inner socket 20 such that myoelectric signals from the stump (not depicted here) can be conducted from the inner side 24 of the inner socket 20 to the outer side 25 of the inner socket 20 through the conductive elements 23. It can likewise be gathered from FIG. 5 that two areas 22 with conductive elements 23 are provided on the inner socket 20, namely arranged medially and laterally. In principle, it is also possible for more than two areas 22 with conductive elements 23 to be arranged on the inner socket 20.

FIG. 6 depicts two views of an electrode 40. The upper illustration shows the outer side of the electrode 40; the lower illustration shows the inner side of the electrode 40. In the installed state, as shown in FIG. 3, the inner side of the electrode 40 is assigned to the area 22 with the conductive elements 23. It is possible to identify sensors or pick-ups on the inner side of the electrode 40; these are embodied in a manner corresponding to the conductive elements 23. By displacing the assembled electrode 40 on the outer socket 10 within the guide 15, it is possible to set a preliminary ideal position of the electrode 40 for obtaining one or more myoelectric signals. To this end, it is not necessary to set surface electrodes on the skin of the patient and already establish an assignment between the position of the electrode and a region on the skin surface. Rather, it is possible to cover a large region of possible derivation points for myoelectric signals by the multiplicity of conductive elements 23, which region is set by the position of the electrode 40 on the outer side 25 of the inner socket 20 in the area 22 of the conductive elements 23, wherein the position of the electrode 40 within the area 22 can be freely selected within the region permitted by the guide 15.

FIGS. 7 and 8 depict a variant of the invention, in which round conductive elements 23 are arranged in the areas 22 on the inner socket 20 instead of the polygonal conductive elements. The electric conductive elements 23 can be inserted retrospectively into the inner socket 20; it is likewise possible for the inner socket 20 to consist of a conductive material which is electrically separated by insulation material. It is likewise possible for conductive silicone or conductive plastic to be arranged in electrically decoupled or insulated regions as conductive elements 23 in the areas 22 so as to form the conductive elements 23 at different positions in the area 22.

The invention claimed is:

1. A prosthetic appliance, comprising:
an outer socket, which has a proximal opening and, at a distal end thereof, a connector for fastening an additional component, the outer socket is formed from a material that is rigid in a longitudinal direction, wherein at least one slit extending at least partially in the longitudinal direction is formed in said outer socket in order to enable a deformation in a radial direction;
an inner socket, which is formed from a flexible material and has a proximal opening;
at least one tensioning appliance, which is fixed on the outer socket and operable to change a diameter of the outer socket; and
at least one electrode displaceably fastened on a side of the outer socket facing the inner socket.

2. The prosthetic appliance as claimed in claim 1, wherein at least one area with conductive elements is provided on the inner socket, which conductive elements conduct myoelectric signals from an inner side of the inner socket to an outer side of the inner socket.

3. The prosthetic appliance as claimed in claim 2, wherein the conductive elements are embedded in the inner socket or the at least one area is embodied as a conductive plastic.

4. The prosthetic appliance as claimed in claim 1, wherein the inner socket is affixed to the outer socket.

5. The prosthetic appliance as claimed in claim 1, wherein the inner socket has a closed cross section.

6. The prosthetic appliance as claimed in claim 1, wherein the inner socket has an open distal end.

7. The prosthetic appliance as claimed in claim 1, wherein the at least one electrode is displaceably mounted and rotatably mounted in at least one guide which is arranged or formed on the outer socket.

8. The prosthetic appliance as claimed in claim 1, wherein the at least one tensioning appliance is embodied as tape or a belt and sets a maximum change in diameter of the outer socket.

9. The prosthetic appliance as claimed in claim 1, wherein the tensioning appliance has a ratchet lock, a lever lock, a rotary clamping lock or a hook-and-loop lock.

10. The prosthetic appliance as claimed in claim 1, wherein the flexible material of the inner socket is embodied to be elastic and stretchable.

11. The prosthetic appliance as claimed in claim 1, wherein the at least one slit forms at least one segment of the outer socket that is connected at the distal end of the outer socket.

12. A prosthetic appliance, comprising:
an outer socket, comprising:
a material that is rigid in a longitudinal direction;
a distal end and a proximal end;
a first proximal opening positioned at the proximal end;
a connector positioned at the distal end, the connector being configured to connect to an additional prosthetic component; and
at least one slit formed in the material of the outer socket and extending at least partially in the longitudinal direction, the at least one slit providing at least one guide positioned on the outer socket;
wherein at least one segment of the material of the outer socket is connected at the distal end of the outer socket and movable radially to change a diameter of the outer socket;
an inner socket comprising a flexible material and a second proximal opening;
at least one tensioning member fixed on the outer socket and operable to change the diameter of the outer socket; and
at least one electrode releasably mounted to the outer socket and arranged facing the inner socket, the at least one electrode extending through the at least one guide.

13. The prosthetic appliance as claimed in claim 12, further comprising a plurality of conductive elements positioned on at least one area of the inner socket, wherein the plurality of conductive elements are configured to conduct myoelectric signals from an inner side of the inner socket to an outer side of the inner socket.

14. The prosthetic appliance as claimed in claim 13, wherein the plurality of conductive elements are embedded in the inner socket or the at least one area is embodied as a conductive plastic.

15. The prosthetic appliance as claimed in claim 12, wherein the inner socket is connected to the outer socket.

16. The prosthetic appliance as claimed in claim 12, wherein the inner socket has a closed cross section.

17. The prosthetic appliance as claimed in claim 12, wherein the inner socket has an open distal end.

18. The prosthetic appliance as claimed in claim 12, wherein the at least one electrode is at least one of displaceably mounted and rotatably mounted in the at least one guide.

19. The prosthetic appliance as claimed in claim 12, wherein the at least one tensioning member is embodied as tape or a belt and defines a maximum change in diameter of the outer socket.

20. The prosthetic appliance as claimed in claim 12, wherein the at least one tensioning member comprises a ratchet lock, a lever lock, a rotary clamping lock, or a hook-and-loop lock.

21. The prosthetic appliance as claimed in claim 12, wherein the at least one slit permits deformation of the outer socket in the radial direction.

22. The prosthetic appliance as claimed in claim 12, wherein the at least one electrode is fastened to the outer socket.

* * * * *